(12) United States Patent
Eckhardt et al.

(10) Patent No.: US 6,599,960 B1
(45) Date of Patent: Jul. 29, 2003

(54) STORAGE-STABLE CATIONCALLY POLYMERIZED PREPARATIONS WITH IMPROVED HARDENING CHARACTERISTICS

(75) Inventors: Gunther Eckhardt, Frieding (DE); Gunther Lechner, Worthsee (DE); Erich Wanek, Kaufering (DE); Ursula Somnitz, Weilheim (DE)

(73) Assignee: Espe Dental AG, Seefeld (DE)

( * ) Notice: Subject to any disclaimer, the term of this patent is extended or adjusted under 35 U.S.C. 154(b) by 0 days.

(21) Appl. No.: 09/555,745

(22) PCT Filed: Dec. 2, 1998

(86) PCT No.: PCT/EP98/07830

§ 371 (c)(1),
(2), (4) Date: Jul. 13, 2000

(87) PCT Pub. No.: WO99/27892

PCT Pub. Date: Jun. 10, 1999

(30) Foreign Application Priority Data

Dec. 2, 1997 (DE) .......................... 197 53 461

(51) Int. Cl.$^7$ .............................. A61C 5/00; A61K 6/10; C08F 2/48; C08G 59/68; C08K 5/098
(52) U.S. Cl. ................. 523/109; 433/217.1; 433/228.1; 522/25; 522/908; 525/533; 525/939; 528/89; 528/90; 528/91; 528/92; 528/95
(58) Field of Search .............................. 528/92, 95, 89, 528/91, 90; 525/437, 533, 939; 523/109; 522/908, 25; 433/217.1, 228.1

(56) References Cited

U.S. PATENT DOCUMENTS

| | | | |
|---|---|---|---|
| 2,803,609 A | * | 8/1957 | Schlenker .................... 528/92 |
| 3,578,633 A | * | 5/1971 | Rossa ........................... 528/95 |
| 3,842,019 A | | 10/1974 | Kropp |
| 3,907,706 A | * | 9/1975 | Robins ..................... 528/89 X |
| 3,960,684 A | * | 6/1976 | Feinberg ................ 525/939 X |
| 4,026,862 A | * | 5/1977 | Smith et al. ............ 525/533 X |
| 4,070,354 A | | 1/1978 | Dick et al. |
| 4,261,871 A | * | 4/1981 | Smith et al. ............... 528/92 X |
| 4,493,911 A | | 1/1985 | Schmitt et al. ............. 523/109 |
| 5,212,261 A | * | 5/1993 | Stierman .................. 528/92 X |
| 5,498,409 A | * | 3/1996 | Hirayama et al. ....... 525/437 X |
| 5,656,703 A | | 8/1997 | Costin et al. ................ 525/531 |
| 6,187,836 B1 | * | 2/2001 | Oxman et al. .......... 523/109 X |

FOREIGN PATENT DOCUMENTS

| | | |
|---|---|---|
| CH | 382918 | 12/1964 |
| DE | 2423552 | 12/1974 |
| DE | A1-4023145 | 1/1992 |
| DE | A1-4324322 | 1/1995 |
| DE | A1-4340949 | 6/1995 |
| DE | 4421623 A1 | 1/1996 |
| DE | A1-4421623 | 1/1996 |
| DE | A1-19534594 | 3/1997 |
| DE | A1-19534664 | 3/1997 |
| DE | A1-19534668 | 3/1997 |
| DE | A1-19648283 | 5/1998 |
| EP | A1083130 | 7/1983 |
| EP | A1083813 | 7/1983 |
| EP | A2110429 | 6/1984 |
| EP | A1279238 | 8/1988 |
| EP | B1119425 | 1/1990 |
| EP | A1697426 | 2/1996 |

OTHER PUBLICATIONS

Database WPI, XP–002100965, Abstract of JP A 60 206825, 1985–10–18.
Database WPI, XP–002114746, Abstract of JP A 52 080399, 1977–07–06.
Database WPI, XP–002100962, Abstract of JP A 61 195158, 1986–08–29.
Database WPI, XP–002100963, Abstract of JP A 07 025989, 1995–01–27.
Database WPI, XP–002100964, Abstract of JP A 60 255820, 1985–12–17.
Database Chemabs, Online! Chemical Abstracts Service, Columbus, Ohio, US; Koyama, Toru et al.: XP002214861, Apr. 9, 1988 (Apr. 9, 1988).

* cited by examiner

Primary Examiner—Richard D. Lovering
(74) Attorney, Agent, or Firm—Birch, Stewart, Kolasch & Birch, LLP

(57) ABSTRACT

The invention relates to preparations with improved curing behavior, which are characterized in that they contain 0.0005 to 50 wt. % of soluble and/or fine-particle organic and/or inorganic alkaline earth and/or alkali metal compounds. The preparations according to the invention may be used for bonding, sealing, casting and coating substrates, also in medical dental and technical dental preparations, and for making impressions of articles and, more particularly, for making dental impressions.

13 Claims, No Drawings

STORAGE-STABLE CATIONCALLY POLYMERIZED PREPARATIONS WITH IMPROVED HARDENING CHARACTERISTICS

This application is the national phase under 35 U.S.C. §371 of PCT International Application No. PCT/EP98/07830 which has an International filing date of Dec. 2, 1998, which designated the United States of America.

The invention relates to storage-stable, cationically polymerisable preparations which have improved curing behaviour. The preparations are based on compounds containing epoxy groups and/or N-alkyl aziridino groups and/or vinyl ether groups.

It is well known that the polymerisation of cationically polymerisable compounds may be initiated by substances with acid properties (H.-G. Elias, "Makromoleküle", Hüthig u. Wepf Verlag (1990)).

It is thus known from U.S. Pat. No. 3,842,019 that sulfonic acid salts such as, for example, $CF_3SO_3Ag$ may be used as latent catalysts for the curing or polymerisation of cationically sensitive monomers, such as, for example, epoxides, vinyl ethers, N-vinyl compounds, aziridines, ethylenically unsaturated hydrocarbons and acetals.

Moreover, curable epoxy compositions are known from EP-A-0 083 130 which contain a metal salt catalyst corresponding to the formula $M(XF_n)_p$ as hardener, wherein M is lithium or a metal of group II, X means boron, arsenic, antimony or phosphorus, n is equal to 4 if n means boron and n is 6 if X means arsenic, antimony or phosphorus, and p is 1 if M means lithium and 2 if M is a metal of group II. The metal salt catalysts are incorporated in the curable composition in a pre-prepared catalyst composition.

Finally, curable epoxy resins are known from JP-A-52080399 which contain imidazolium salts and anion acceptors, such as, for example, metals, carboxylic acid salts of metals, etc., for improving curing.

It is important for the use of cationically polymerisable preparations that polymerisation begins at the desired time and is ended with a curing pattern that depends on the application in question.

For the production, storage and use of cationically polymerisable preparations, it is necessary to prevent unwanted premature polymerisation and to obtain the desired pattern of the degree of conversion/time curve after initiation.

The object is achieved by cationically polymerisable preparations which are characterised in that they contain 0.0005 to 50 wt. % of soluble and/or fine-particle organic and/or inorganic alkaline earth and/or alkali metal compounds.

Surprisingly, it was ascertained that the retarding effect of the soluble and/or fine-particle organic and/or inorganic alkaline earth and/or alkali metal compounds is greatly reduced as polymerisation proceeds. This retarding effect at the beginning of cationic polymerisation and its reduction as polymerisation proceeds may be utilised both to prolong the pot life once initiation has taken place and to produce storage-stable cationically polymerisable preparations without the disadvantage of a reduced degree of conversion. The use according to the invention of the above-mentioned alkaline earth and/or alkali compounds permits the production of storage-stable cationically polymerisable preparations and, moreover, adjustment of the curing pattern and, more particularly, of the pot life of the initiated preparation at ambient temperature and of the time required to achieve further processability of the cured material.

The cationically polymerisable compounds according to the invention are based preferably on monomers containing epoxy groups and/or N-alkyl aziridino groups and/or vinyl ether groups.

Suitable monomers containing epoxy groups are aromatic, aliphatic and cycloaliphatic epoxy compounds. Typical representatives of said monomers are the glycidyl ethers of bisphenols or novolaks and of aliphatic alkanols, alkane diols or polyether diols.

The monomers containing cycloaliphatic epoxy groups are selected preferably from the group (1) comprising the diepoxides of cycloaliphatic esters having the general structure

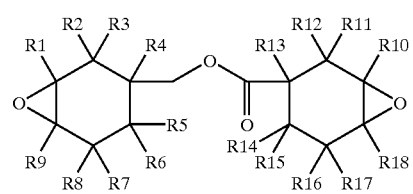

wherein the substituents $R_1$ to $R_{18}$ may be the same or different and independently of one another mean H, alkyl with 1 to 12 carbon atoms or aryl with 6 to 15 carbon atoms, (2) comprising products of the reaction of epoxidised cyclohexane derivatives of the alcohol and acid type with aliphatic dicarboxylic acids or diols and (3) comprising cycloaliphatically substituted dioxyspiro alkanes.

Cycloaliphatic diepoxy compounds used in particular preference are 3,4-epoxycyclohexylmethanol-3',4'-epoxycyclohexylcarboxylate and 3-(3',4'-epoxycyclo-(hexyl)-8,9-epoxy-2,4-dioxyspiro(5,5)undecane.

These and other cycloaliphatic diepoxides which may be used according to the invention are described, for example, in EP-B-0 119 425.

The production and cationic polymerisation of N-alkylaziridino compounds is by no means new and is summarised by H. Bestian in "Methoden der Organischen Chemie" (Houben Weyl) XII/1 (1958). DE-C-17 45 810 describes the synthesis of aziridino polyethers and the production of moulded articles on the basis of cationic polymerisation of said aziridino polyethers. Aziridino polyethers are used in dental preparations and, more particularly, in impression materials.

The cationic polymerisability of vinyl ethers is by no means new and is utilised nowadays for surface treatment, for example, in coating compounds with very high reactivity. Typical representatives of monomeric vinyl ethers are: monovinyl ethers of aliphatic, branched and unbranched alcohols such as n-butylvinyl ether, octadecylvinyl ether, cyclohexylvinyl ether, tert.-amylvinyl ether, butane diol monovinyl ether, divinyl ethers of ethylene glycol and various oligoethylene glycols, and hexane diol and trivinyl ethers of trimethylol propane.

The types mentioned and individual representatives of cationically polymerisable monomers may be used on their own and in mixture.

When making a selection, however, both the differing reactivity and the complicating factor that cationic polymerisation may take place at different calionic centres have to be taken into account.

The preparations according to the invention also contain the compounds suitable for initiating polymerisation. Depending on the number of components into which the preparations have to be divided up in order to obtain sufficient storage stability, and depending on the properties of the monomers, various classes of compounds may be considered.

Using soluble and/or fine-particle organic and/or inorganic alkaline earth and/or alkali compounds according to the invention, it is possible to produce one-component storage-stable preparations containing both the individual monomers described or mixtures of individual types of monomers and individual representatives as well as photoinitiators of the onium compound and/or metallocenium compound type—in each case with a complex anion having a weak nucleophilic effect.

Typical representatives of onium compounds which decompose on irradiation with light in a wave length from 280 to 400 nm are bisaryliodonium compounds and trisarylsulfonium compounds.

The metallocenium cation may have a variety of structures, as shown, for example, in EP-A-0 542 716. For use in the materials according to the invention, however, it is expedient to select those cations which decompose to form Lewis acids or Brönsted acids on irradiation with light in a wave length from 300 to 550 nm. This condition may be fulfilled in an industrially useful manner by metallocenium compounds with iron as the central atom.

The anions used may be, for example, the hexafluorophosphate or the hexafluoroantimonate anion. Also suitable are complex borate anions having the general structure

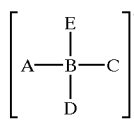

wherein the substituents A, E, C, D may be the same or different and mean aryl or perfluoroaryl. An anion used in preference is tetrakis(pentafluorophenyl)borate.

The compounds used as photoinitiators are used preferably in concentrations from 0.1 to 2 wt. %, particularly preferably 0.4 to 1.0 wt. %, of the preparations in question.

The one-component preparations containing alkaline earth and/or alkali compounds according to the invention are characterised by good storage stability, which may be adjusted to values between 12 and 60 months at 23° C. by means of the nature and concentration of the alkaline earth and/or alkali compounds.

If necessary from a technological angle, the duration of the retardation period after irradiation of the preparations at the start of polymerisation may be adjusted to the desired value by means of the nature and concentration of the alkaline earth and/or alkali compounds. The required curing rate after retardation can be achieved by a sufficient photoinitiator concentration and optionally by the use of moderately elevated temperatures. By adding alkaline earth and/or alkali compounds is it thus possible to formulate one-component, cationically curing preparations which have sufficient storage stability and whose curing pattern may be adjusted to the application in question.

The cationically polymerisable preparations may be divided into two partial preparations, the so-called catalyst component containing the polymerisation-initiating species, optionally in a diluent, and the so-called base component containing the monomers. The alkaline earth and/or alkali compounds to be used according to the invention may be added both to the catalyst component and to the base component. The addition to the base component is the preferred embodiment.

In principle, Brönsted and/or Lewis acids may be used in the catalyst component in the case of a two-component embodiment. Suitable acids are, for example, hexafluoroantimonic acid, hexafluorophosphoric acid, tetrafluoroboric acid, p-toluenesulfonic acid, benzenesulfonic acid and alkane sulfonic acids.

It is also possible, however, to use systems whose individual components are divided into partial preparations and which, when the partial preparations are mixed, produce the actual polymerisation-initiating species such as, for example, the acids. For example, non photosensitive sulfonium compounds as described in DE-A-25 15 593 may be used in the catalyst component, which, after contact with the aziridino compound of the base component, form a polymerisation-initiating species of the aziridinium salt type.

Moreover, the catalyst component may contain aziridinium salts which are suitable for initiating cationic polymerisation of the appropriately selected monomers. Suitable aziridinium salts may be obtained by reaction of aziridino compounds with the above-mentioned acids.

The cationically curing, one-component or two-component preparations contain, according to the invention, 0.0005 to 50 wt, % of alkaline earth and/or alkali compounds.

The alkaline earth and alkali metal compounds may be introduced in the dissolved and in the fine-particle solid form into the preparations. It is also possible according to the invention to use inorganic fillers doped with alkaline earth and/or alkali metal compounds or containing alkaline earth and/or alkali ions, such as silicates, quartz, diatomaceous earth or fine-particle organic polymers which contain alkali compounds in the adsorbed form or the alkali metal ions in the bound form.

Soluble organic and/or inorganic alkaline earth and/or alkali metal compounds with molecular weights below 1000 g/mole are used preferably in an amount from 0.01 to 20 wt. %. Moreover, the use of high polymer compounds in an amount from 1 to 50 wt. % with an alkaline earth and/or alkali content from 0.01 to 10 wt. % is preferred.

The use of alkali metal alkyl compounds such as, for example, butyllithium is possible. It is preferable, however, to use alkaline earth and/or alkali metal alcoholates of the kind that may be obtained by reaction of selected, preferably primary monohydric or polyhydric alcohols to the corresponding alkylates.

Typical representatives of this class of compound are: lithium-2-ethylhexylalcoholate, lithiumlauryl alcoholate, sodium alcoholate of polytetrahydrofuran diol with a molecular weight of 350 g/mole, lithium alcoholate of a mixed polyether glycol of tetrahydrofuran and ethylene oxide units with a molecular weight from 3000 to 8000 and preferably 6000 g/mole.

A particularly preferred class of compound of alkaline earth and alkali compounds is that of the alkaline earth and/or alkali salts of saturated or unsaturated carboxylic acids, which carboxylic acids may be mono or polyvalent and aliphatic, olefinic or aromatic. Typical representatives of this class of compound are: calcium stearate, calcium oleate, strontium oleate, lithium-2-ethylhexanolate, sodium palmitate, sodium stearate, potassium erucate, sodium ricinolate, lithium oleate, lithium dodecyl benzoate. This class of compound also includes the alkaline earth and/or alkali metal carboxylates of saturated or unsaturated carboxylic acids which may be obtained from oligomeric monovalent and preferably polyvalent acids and the corresponding hydroxides, alkyls or alkoxides. All these compounds are used in amounts from preferably 0.01 to 20 wt. %.

Such oligomeric acids may be, for example, carboxylfunctionalised polyethers, polyesters or acrylonitrile-butadiene copolymers with molecular weights from 500 to 5000 g/mole. Alkali carboxylates which may be used to advantage because they are freely soluble in the base paste may be obtained from polyether or polyester polyols by complete or partial reaction of the OH groups with the anhydride of a divalent acid followed by neutralisation with alkali hydroxides, alkali alkyls or alkali alkoxides.

A typical representative of this class of compounds is the reaction product of a caprolactone triol with the molecular weight 540 g/mole with maleic anhydride in the ratio of OH groups to anhydride groups of 1:0.4, which is subsequently converted with lithium hydroxide or lithium alkoxide to the lithium carboxylate.

Moreover, 0.01 to 20 wt. % of alkaline earth and/or alkaline earth salts of the reaction products of cyclic anhydrides with mono and/or polyhydric alcohols are used in preference, maleic anhydride being the preferred cyclic anhydride and triols with molecular weights above 500 g/mole being preferred polyhydric alcohols for the reaction. In preference, the reaction of the OH groups of the triols with maleic anhydride takes place only partially.

Preferred alkali metal compounds are those of potassium, sodium and/or lithium, more particularly lithium. Preferred alkaline earth metal compounds are those of calcium and strontium.

The alkaline earth and/or alkali compounds adsorbed on a solid or the fillers containing alkaline earth and/or alkali ions are introduced in portions into the base component preferably towards the end of the mixing process. The addition of some alcoholates or carboxylates takes place advantageously as a pre-prepared paste.

For example, calcium stearate, calcium oleate, sodium palmitate, lithium ricinolate, lithium erucate or lithium oleate may be kneaded in polyether glycols optionally with the addition of water and brought to a pasty consistency by means of a dissolver or in a roll mill.

The addition of these retarder pastes may be carried out at any time during base component production, but is carried out advantageously towards the end of kneading.

The invention is explained in more detail on the basis of the examples below.

The preparations according to the invention may be used for bonding, sealing, casting and coating substrates, also in medical dental and technical dental preparations, and for making impressions of articles and, more particularly, for making dental impressions.

EXAMPLES

Examples 1 to 4

Examples 1 to 4 relate to one-component preparations, whereas two-component preparations are described in examples 5 to 15.

The assessment of the storage stability of the monomer-containing preparations was carried out by viscosity measurements and inspection of curing. The storage stability was determined at 23° C. and given in months. Within the stated period, the viscosity of the monomer-containing preparation rose by less than 15% compared with the starting value, and the curing rate and the properties of the cured material did not alter.

The "onset of polymerisation" was defined as the time when an irradiated one-component preparation or a mixed two-component preparation exhibits pronounced changes such as skin formation, cobwebbing and greatly reduced flowability. The time until the "onset of polymerisation" is regarded as the "pot life".

The "end of polymerisation" is defined as the time at which, after irradiation has begun, the irradiated one-component preparation or, after mixing has begun, the mixed two-component preparation has solidified to such an extent that the solid obtained withstands the conventional mechanical stresses relating to manufacture and is "suitable for further processing". Normally, the internal strength of the solid at this time has risen to about 50 to 80% of the final value. The final values of the mechanical properties are mostly achieved only after several hours.

In order to cure the one-component preparations, these were irradiated in a circular Teflon mould with a 2 mm specimen height and a diameter of 20 mm with a lamp emitting light in the wave length range from 280 to 550 mm, the intensity of radiation on the plane of the specimen surface having a value of 45 mW/cm$^2$.

The irradiation time at which the described signs of the "onset of polymerisation" occurred was determined with a spatula by repeated immersion in the irradiated preparation. In order to determine the "end of polymerisation", irradiation was continued for a further 30 seconds beyond the "onset of polymerisation".

Five minutes after irradiation commenced, the specimen was removed from the mould and its strength assessed.

For more accurate measurements, small test rods with the test surface dimensions 10×2×2 mm were prepared on the basis of the irradiation method described. The minimum strength required is strongly dependent on the application in question.

The examination of the specimens according to examples 1 to 4 resulted in tensile strength values at the "end of polymerisation" which were greater than 2 N/mm$^2$.

TABLE 1

Composition of the one-component preparations according to the invention

| Ex. | Monomers | Wt. % | Stabilisers/retarders according to the invention | Wt. % | Other constituents | Wt. % |
|---|---|---|---|---|---|---|
| 1 | 3,4-epoxycyclohexyl-methyl-3',4'-epoxyhexyl carboxylate | 57.43 | Reaction product of poly-caprolactone triol (molecular wt. 540 g/mole) with maleic anhydride in the molar ratio 1:0.4 followed by neutralisation with lithium methylate | 0.11 | Polycaprolactone triol (M = 540 g/mole) 8-Hydroxyquinoline Ferrocenium hexafluoroantimonate Cumene hydroperoxide (80%) | 38.9 0.01 0.70 2.85 |
| 2 | Trisaziridino polyether with an imino equivalent mass of 2050, containing ethylene oxide and tetrahydrofuran units in the ratio 1:3.4 | 60.15 | Reaction product of a mixed polyether diol with the molecular wt. 5900 g/mole containing ethylene oxide and tetrahydrofuran units in the ratio 1:3.4 with butyl lithium | 5.7 | Dibenzyl toluene Ferrocenium tosylate Cumene hydroperoxide Synthetic silica flour, silanised | 11.70 1.45 0.50 20.50 |

TABLE 1-continued

Composition of the one-component preparations according to the invention

| Ex. | Monomers | Wt. % | Stabilisers/retarders according to the invention | Wt. % | Other constituents | Wt. % |
|---|---|---|---|---|---|---|
| 3 | 3,4-epoxycyclohexyl-methyl-3',4'-epoxyhexyl carboxylate | 4.7 | Reaction product as in example 1 but neutralised with sodium methylate | 0.07 | Mixed polyether diol with a molecular wt. of 5900 g/mole, containing ethylene oxide and tetrahydrofuran units in the ratio 1:3.4 | 10.1 |
|   | Divinyl ether of 1,4-cyclo-hexane dimethanol | 84.33 | | | Trisarylsulfonium hexafluoroantimonate | 0.8 |
| 4 | 3,4-epoxycyclohexyl-methyl-3',4'-epoxyhexyl carboxylate | 31.7 | Reaction product of polyethylene glycol dicarboxylic acid with a molecular wt. of 600 with lithium hydroxide | 0.09 | Polycarbonate diol with a molecular wt. of 550 g/mole | 5.86 |
|   | Epoxidised polybutadiene with an epoxy equivalent mass of 450 g/mole | 20.1 | | | Trisarylsulfonium hexafluoroantimonate | 1.25 |
|   | | | | | Synthetic silica flour, silanised | 41.0 |

TABLE 2

Test results of the preparations according to examples 1 to 4
(see Table 1)

| Preparation acc. to example | Storage stability at 23° C./months | "Onset of polymerisation" seconds | "End of polymerisation" seconds |
|---|---|---|---|
| 1 | More than 24 | 18 | 20 |
| 2 | More than 24 | 40 | 80 |
| 3 | 18 | 13 | 16 |
| 4 | 18 | 11 | 13 |

Comparison Examples 1 to 4

The production of the preparations according to examples 1 to 4 was repeated except that in each case the stabilisers/retarders according to the invention were omitted.

Comparison Example 5

In order to produce the preparation according to comparison example 5, the stabiliser/retarder according to the invention in the formulation of example 1 was replaced by butoxyethyl-4-dimethylaminobenzoate in the same concentration.

The preparations thus obtained according to comparison examples 1 to 5 were cured under the same conditions as for examples 1 to 4.

The test results of comparison examples 1 to 5 are summarised in Table 3.

TABLE 3

Test results of the preparations according to comparison examples 1 to 5

| Preparation according to comparison example | Storage stability at 23° C./ months | "Onset of polymerisation" seconds | "End of polymerisation" seconds |
|---|---|---|---|
| 1 | 8 | 12 | 15 |
| 2 | 12 | 10 | 60 |
| 3 | 6 | 10 | 12 |
| 4 | 3 | 8 | 12 |
| 5 | 18 | 16 | 36 |

The comparison of the results of examples 1 to 4 with those of comparison examples 1 to 5 shows that an improvement in storage stability can be achieved both with the compounds used according invention and with an amine (comparison example 5). The compounds used according to the invention bring about an extension in the pot life which is relevant for processing purposes with only a slightly prolonged "end of polymerisation", whereas the "end of polymerisation" is greatly retarded by the use of an amine.

TABLE 4

Composition of the two-component preparations according to the invention
Part: catalyst components (wt. %)

| Catalyst component | Polymerisation-initiating species or part of 2-pack initiating system | Wt. % | Other constituents | Wt. % |
|---|---|---|---|---|
| Component 1 | Hexafluoroantimonic acid | 0.3 | Polycaprolactone triol with a molecular wt. of 540 g/mole | 98.8% |
|   | | | Pigment paste, red | 0.2 |
|   | | | Hydrophilic, pyrogenic silica | 0.7 |
| Component 2 | Bis-aziridinium-hexafluoroantimonate of a mixed polyether diol with a molecular wt. of 5900 g/mole containing ethylene oxide and tetrahydrofuran units in the ratio 1:3.4 | 64.0 | Polypropylene glycol with a molecular wt. of 3000 | 35.7 |
|   | | | Pigment paste, red | 0.3 |

TABLE 4-continued

Composition of the two-component preparations according to the invention
Part: catalyst components (wt. %)

| Catalyst component | Polymerisation-initiating species or part of 2-pack initiating system | Wt. % | Other constituents | Wt. % |
|---|---|---|---|---|
| Component 3 | Hexafluoroantimonic acid | 0.5 | Mixed polyether diol with a molecular wt. of 5900 g/mole containing ethylene oxide and tetrahydrofuran units in the ratio 1:3.4 | 99.2 |
|  |  |  | Pigment paste, red | 0.3 |
| Component 4 | Toluenesulfonic acid monohydrate | 10.0 | Polypropylene glycol with a molecular wt. of 8000 g/mole | 20.0 |
|  |  |  | Poly(ethylene, propylene) glycol with a molecular wt. of 3000 g/mole | 62.5 |
|  |  |  | Hydrophilic pyrogenic silica | 7.0 |
|  |  |  | Pigment paste, red | 0.5 |
| Component 5 | p-Toluenesulfonic acid monohydrate | 9.0 | Poly(ethylene, propylene) glycol with a molecular wt. of 3000 g/mole | 82.5 |
|  |  |  | Hydrophilic pyrogenic silica | 8.0 |
|  |  |  | Pigment paste, red | 0.5 |

TABLE 5

Composition of the two-component preparations according to the invention;
Part: base components and their storage stability (wt. %)

| Base component | Monomers | Wt. % | Stabilisers/retarders acc. to invention | Wt. % | Others | Wt. % | Storage stability at 23° C./mths |
|---|---|---|---|---|---|---|---|
| B1 | 3,4-epoxycyclohexylmethyl-3',4'-epoxycyclohexyl carboxylate | 93.38 | Reaction product of a polycaprolactone triol with a mol. wt. of 540 g/mole with maleic anhydride in the molar ratio 1:0.35 followed by neutralisation with lithium methylate | 0.12 | Finely dispersed silica. silanised | 2.1 | >18 |
|  | Hydroxybutylvinylether | 3.7 |  |  | Pigment paste, blue | 0.7 |  |
| B2 | 3,4-epoxycyclohexylmethyl-3',4'-epoxycyclohexyl carboxylate | 75.55 | Reaction product of a polycaprolactone triol with a mol. wt. of 540 g/mole with maleic anhydride in the molar ratio 1:0.35 followed by neutralisation with lithium methylate | 0.05 | Finely dispersed silica. silanised | 1.7 | >18 |
|  | Glycidyloxypropyltrimethoxy silane | 1.0 |  |  | Synthetic silica flour. silanised | 21.0 |  |
|  |  |  | Calcium stearate | 0.10 | Pigment paste, blue | 0.6 |  |
| B3 | Bis-N-alkylaziridino derivative of a mixed polyether with a mol. wt. of 6100 containing ethylene oxide and tetrahydrofuran units in the ratio 1:3.6 | 58.6 | Lithium oleate | 2.0 | Mixed polyether glycol with a mol. wt. of 5900 | 3.5 | >24 |
|  |  |  |  |  | Hydrog. beef tallow | 11.2 |  |
|  |  |  |  |  | Diatomaceous earth | 14.3 |  |
|  |  |  |  |  | Dibenzyltoluene |  |  |
|  |  |  |  |  | Pigment paste, blue | 10.4 |  |
|  |  |  |  |  |  | 0.7 |  |
| B4 | Bis-N-alkylaziridino derivative of a mixed polyether with a mol. wt. of 6100 containing ethylene oxide and tetrahydrofuran units in the ratio 1:3.6 | 57.3 | Calcium stearate | 1.5 | Poly(ethylene, propylene) glycol | 8.3 | >24 |
|  |  |  | Reaction product of a mixed polyether polyol with butyl lithium; lithium equivalent wt.: 2100 g/mole | 5.0 | Hydrog. beef tallow | 11.7 |  |
|  |  |  |  |  | Diatomaceous earth | 14.3 |  |
|  |  |  |  |  | Dibenzyltoluene | 1.2 |  |
|  |  |  |  |  | Pigment paste, blue | 0.7 |  |
| B5 | 3,4-epoxycyclohexylmethyl-3',4'-epoxycyclohexyl carboxylate | 68.7 | Glass powder treated with hydrochloric acid, washed with water, stored for 24 hours in a 0.5% alcoholic solution of lithium hydroxide, dried | 22.1 | Finely dispersed silica. silanised | 3.2 | >12 |
|  | Bis-N-alkylaziridino derivative of a mixed polyether with a mol. wt. of 6100 containing ethylene oxide and tetrahydrofuran units in the ratio 1:3.6 | 5.3 |  |  | Pigment paste, blue | 0.7 |  |

TABLE 6

Composition of the two-component preparations according to the invention and test results

| Example | Catalyst component (see Table 4) | Base component (see Table 5) | Mixing ratio (acc. to weight) | "Onset of polymerisation" seconds | "End of polymerisation" seconds |
|---|---|---|---|---|---|
| 5 | C.1 | B1 | 1:1.2 | 20 | 600 |
| 6 | C.1 | B2 | 1:1.2 | 15 | 550 |
| 7 | C.2 | B3 | 1:5 | 45 | 180 |
| 8 | C.2 | B4 | 1:5 | 60 | 210 |
| 9 | C.3 | B5 | 1:2 | 125 | 430 |

TABLE 6-continued

Composition of the two-component preparations according to the invention and test results

| Example | Catalyst component (see Table 4) | Base component (see Table 5) | Mixing ratio (acc. to weight) | "Onset of polymerisation" seconds | "End of polymerisation" seconds |
|---|---|---|---|---|---|
| 10 | C.4 | B3 | 1:4.5 | 140 | 350 |
| 11 | C.4 | B4 | 1:5 | 150 | 390 |
| 12 | C.4 | B4 | 1:4 | 120 | 360 |
| 13 | C.5 | B3 | 1:4 | 110 | 350 |
| 14 | C.5 | B3 | 1:5 | 130 | 370 |
| 15 | C.5 | B4 | 1:4.5 | 125 | 340 |

Examples 5 to 15

The two-component preparations according to examples 5 to 15 were produced by mixing the catalyst components (Table 4) and the base components (Table 5) in accordance with the mixing ratio given in Table 6 and the time until the "onset of polymerisation" and until the "end of polymerisation" was determined in the manner described, the mixing time in examples 5 and 6 being 10 seconds and in examples 7 to 15 being 30 seconds. The results of the determination of the characteristics of the curing pattern are shown in Table 6. The storage stability of the base components for the production of the two-component preparations according to examples 5 to 15 is shown in Table 5.

Comparison Examples 6 to 16

In order to produce the two-component preparations according to comparison examples 6 to 16, the catalyst components according to Table 4 were mixed in the mixing ratios stated in Table 6 with the base components according to Table 5 except that the stabilisers according to the invention in the base pastes were omitted for the preparations of the comparison examples. The storage stability of the base components without the stabilisers according to the invention was 4 to 10 months at 23° C.

Table 7 contains a summary of the characteristics for the curing pattern of the preparations according to comparison examples 6 to 16.

57.4 wt. % of bis-N-alkylaziridinopolyether according to B4

0.5 wt. % of 1-laurylimidazole 42.1 wt. % of other constituents in the ratio given as for the base component B4.

An "onset of polymerisation" of 140 seconds and an "end of polymerisation" of 450 seconds was determined.

The storage stability of the base components was 24 months.

A comparison of the results of the base components used for examples 5 to 15 (Table 5) with those of comparison examples 6 to 16 shows that the storage stability of the base components is improved both with the compounds used according to the invention and with an amine (see comparison example 17).

The compounds used according to the invention bring about a prolongation of the time until the "onset of polymerisation" which is very important for processing, with a tolerable, prolonged "end of polymerisation", whereas the "end of polymerisation" is retarded to a much greater extent by the use of the amine (comparison example 17).

What is claimed is:

1. A cationically polymerizable dental preparation based on monomers which are selected from the group consisting of N-alkylaziridine group-containing monomers and epoxy-containing monomers, wherein the preparation contains 0.0005 to 50 wt. %. of soluble and/or fine-particle organic and/or inorganic alkaline earth and/or alkali metal com-

TABLE 7

Comparison examples 6 to 16
Composition of the two-component preparations and summary of the test results

| Comparison example | Catalyst component (see Table 4) | Base component a) (see Table 5) | Mixing ratio (acc. to wt.) | "Onset of polymerisation" seconds | "End of polymerisation" seconds |
|---|---|---|---|---|---|
| 6 | C.1 | B1 | 1:1.2 | <10 (even during mixing) | 400 |
| 7 | C.1 | B2 | 1:1.2 | <10 (even during mixing) | 300 |
| 8 | C.2 | B3 | 1:5 | 25 | 150 |
| 9 | C.2 | B4 | 1:5 | 40 | 170 |
| 10 | C.3 | B5 | 1:2 | 30 | 125 |
| 11 | C.4 | B3 | 1:4.5 | 48 | 245 |
| 12 | C.4 | B4 | 1:5 | 53 | 255 |
| 13 | C.4 | B4 | 1:4 | 45 | 240 |
| 14 | C.5 | B3 | 1:4 | 42 | 205 |
| 15 | C.5 | B3 | 1:5 | 48 | 220 |
| 16 | C.5 | B4 | 1:4.5 | 52 | 260 | a) in each case without the stabiliser (retarder) according to the invention

Comparison Example 17

The catalyst component C.5 (see Table 4) was mixed in a weight ratio of 1:5 with a base component containing:

pounds in order to adjust the curing behavior and to improve the storage stability, wherein the preparation consists of a base component and, separately therefrom, a catalyst component, wherein the base component contains the monomer(s) and the catalyst component contains the species initiating polymerization, optionally in a diluent, and wherein the alkaline earth and/or alkali compounds are present in the base and/or catalyst component, and wherein the preparation further comprises a polymerization-initiating substance or a substance from which a polymerization-initiating substance is produced.

2. The preparation according to claim 1, wherein the preparation contains soluble organic and/or inorganic alkaline earth and/or alkali metal compounds with molecular weights below 10,000 g/mole in an amount from 0.01 to 20 wt. %.

3. The preparation according to claim 1, wherein the preparation contains soluble high polymer compounds in an amount from 1 to 50 wt. % which have an alkaline earth and/or alkali metal content from 0.01 to 10 wt. %.

4. The preparation according to claim 1, wherein the preparation contains 0.01 to 20 wt. % of alkaline earth and/or alkali metal carboxylates.

5. The preparation according to claim 1, wherein the preparation contains 0.01 to 20 wt. % of alkaline earth and/or alkali salts of saturated or unsaturated carboxylic acids.

6. The preparation according to claim 1, wherein the preparation contains 0.01 to 20 wt. % of alkaline earth and/or alkali salts of the reaction products of cyclic anhydrides with mono- and/or polyhydric alcohols.

7. The preparation according to claim 6, wherein the cyclic anhydride used for the reaction is maleic anhydride.

8. The preparation according to claims 6 or 7, wherein the polyhydric alcohols used for the reactions are triols with molecular weights above 500 g/mole.

9. The preparation according to claim 8, wherein the reaction of the OH groups of the triols with maleic anhydride takes place only partially.

10. The preparation according to claim 1, wherein the alkali metal compounds the preparation contains are those of potassium, sodium, lithium, or combinations thereof, and/or the alkaline earth compounds the preparation contains are those of calcium, strontium, or combination thereof.

11. The preparation according to claim 10, wherein the alkali metal compound the preparation contains is lithium.

12. The preparation according to claim 1, wherein the preparation further comprises an effective amount of one or more photoinitiators.

13. The preparation according to claim 1, wherein the alkaline earth and/or alkali compounds are present in the base component.

* * * * *

UNITED STATES PATENT AND TRADEMARK OFFICE
CERTIFICATE OF CORRECTION

PATENT NO.         : 6,599,960 B1
APPLICATION NO. : 09/555745
DATED                  : July 29, 2003
INVENTOR(S)       : Gunther Eckhardt It is certified that error appears in the above-identified patent and that said Letters Patent is hereby corrected as shown below:

First page, Column 1, in the title, delete "CATIONCALLY POLYMERIZED" and insert --CATIONICALLY POLYMERISED--, therefor.

First page, Column 2, under Foreign Patent Documents, delete "DE    4421623 A1    1/1996".

Column 1
Lines 1-2, delete "CATIONCALLY POLYMERIZED" and insert --CATIONICALLY POLYMERISED--, therefor.

Line 44, the following two paragraphs should be inserted:
   --It is well known that cationic polymerisation is retarded or prevented by basic substances. So it is known (DE-A-195 34 594) to obtain a stabilising effect by adding nitrogen-containing compounds and, more particularly, amines. Amines usually have sufficient solubility in the preparations to be stabilised, and retard polymerisation. The retarding effect of amines is, however, present throughout the curing time and usually leads to a reduced degree of conversion of the cationically polymerisable groups, which is usually associated with impaired mechanical properties of the cured materials.
   The object of the present invention is to provide cationically polymerisable preparations which are stable in storage, on the one hand, and in which the stabilisers responsible for the storage stability do not, on the other hand, impede polymerisation in an undesirable manner.--

Column 2
Line 57, delete "calionic" and insert --cationic--, therefor.

Column 8
Line 43, after "according" insert --to the--.

UNITED STATES PATENT AND TRADEMARK OFFICE
CERTIFICATE OF CORRECTION

PATENT NO. : 6,599,960 B1
APPLICATION NO. : 09/555745
DATED : July 29, 2003
INVENTOR(S) : Gunther Eckhardt It is certified that error appears in the above-identified patent and that said Letters Patent is hereby corrected as shown below:

<u>Columns 9-10</u>
Column 6, row 1 (Table 5), line 1, delete "silica." and insert --silica,--, therefor.
Column 6, row 2 (Table 5), line 1, delete "silica." and insert --silica,--, therefor.
Column 6, row 2 (Table 5), line 3, delete "flour." and insert --flour,--, therefor.
Column 6, row 5 (Table 5), line 1, delete "silica," and insert --silica,--. therefor.

<u>Column 12</u>
Line 42, in Claim 1, delete "%." and insert --%--, therefor.

Signed and Sealed this

First Day of April, 2008

JON W. DUDAS
*Director of the United States Patent and Trademark Office*